US010575832B2

(12) United States Patent
Imai et al.

(10) Patent No.: US 10,575,832 B2
(45) Date of Patent: Mar. 3, 2020

(54) BIOPSY NEEDLE DEVICE

(71) Applicant: MEDFORCE JAPAN CO., LTD., Utsunomiya-shi, Tochigi (JP)

(72) Inventors: Takanori Imai, Utsunomiya (JP); Hiroshi Hirota, Nasushiobara (JP)

(73) Assignee: Medforce Japan Co., LTD., Utsunomiya-shi (JP)

( * ) Notice: Subject to any disclaimer, the term of this patent is extended or adjusted under 35 U.S.C. 154(b) by 0 days.

(21) Appl. No.: 15/502,673

(22) PCT Filed: May 13, 2016

(86) PCT No.: PCT/JP2016/064224
§ 371 (c)(1),
(2) Date: Feb. 8, 2017

(87) PCT Pub. No.: WO2016/182043
PCT Pub. Date: Nov. 17, 2016

(65) Prior Publication Data
US 2017/0231607 A1    Aug. 17, 2017

(30) Foreign Application Priority Data

May 13, 2015   (JP) ................................. 2015-097973

(51) Int. Cl.
*A61B 10/02*      (2006.01)
(52) U.S. Cl.
CPC .......... *A61B 10/0266* (2013.01); *A61B 10/02* (2013.01); *A61B 10/0275* (2013.01); *A61B 10/0283* (2013.01); *A61B 2010/0208* (2013.01)

(58) Field of Classification Search
None
See application file for complete search history.

(56) References Cited

U.S. PATENT DOCUMENTS 5,159,933 A     11/1992  Hut
5,400,798 A *   3/1995   Baran ................ A61B 10/0275
                                                         600/567
2001/0009979 A1  7/2001  Weilandt et al.
(Continued)

FOREIGN PATENT DOCUMENTS

JP       H03-500018 A    1/1991
JP       H06-28663 B2    4/1994
(Continued)

OTHER PUBLICATIONS

Jul. 19, 2016 Search Report issued in International Patent Application No. PCT/JP2016/064224.

*Primary Examiner* — Sean P Dougherty
*Assistant Examiner* — Benjamin S Melhus
(74) *Attorney, Agent, or Firm* — Oliff PLC

(57) ABSTRACT

A biopsy needle device constructed in a manner such that an internal needle is triggered in response to unlocking operation of internal needle locking device, after which a piston is retracted by a piston retraction spring in response to unlocking operation of piston locking device, whereby negative pressure is generated in a recess of the internal needle resulting in suction of biological tissue into the recess, and an external needle is triggered in response to unlocking operation of external needle locking device, thereby cutting and sampling the biological tissue which has been drawn into the recess.

5 Claims, 8 Drawing Sheets

(56) References Cited

U.S. PATENT DOCUMENTS

| | | |
|---|---|---|
| 2002/0082519 A1 | 6/2002 | Miller et al. |
| 2006/0173377 A1 | 8/2006 | McCullough et al. |
| 2011/0208087 A1* | 8/2011 | Trezza, II .......... A61B 10/0275 600/567 |
| 2015/0057571 A1 | 2/2015 | Gundberg |
| 2015/0238171 A1* | 8/2015 | Shabaz .............. A61B 10/0275 600/567 |
| 2016/0262733 A1* | 9/2016 | Schlarb ............. A61B 10/0275 |

FOREIGN PATENT DOCUMENTS

| | | |
|---|---|---|
| JP | H06-83006 U | 11/1994 |
| JP | H07-289555 A | 11/1995 |
| JP | 2004-519279 A | 7/2004 |
| JP | 2006-081889 A | 3/2006 |
| JP | 2007-313332 A | 12/2007 |
| JP | 2008-528208 A | 7/2008 |
| JP | 2014-534879 A | 12/2014 |

* cited by examiner

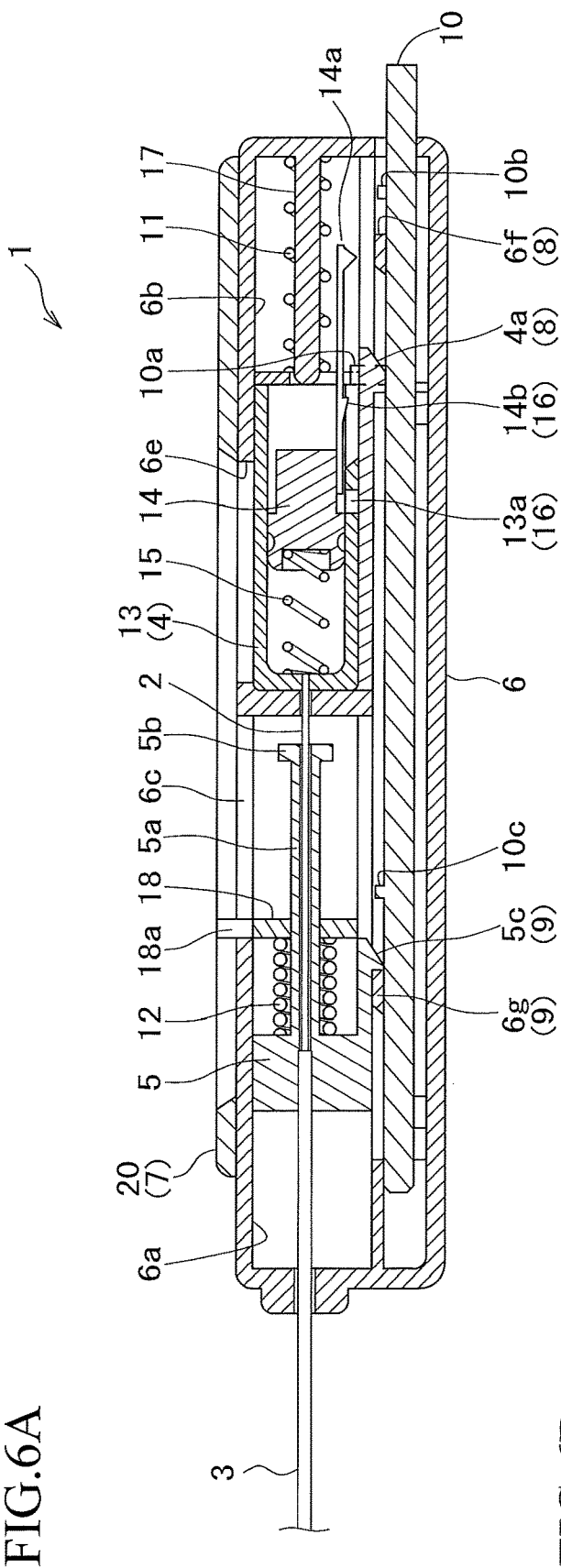
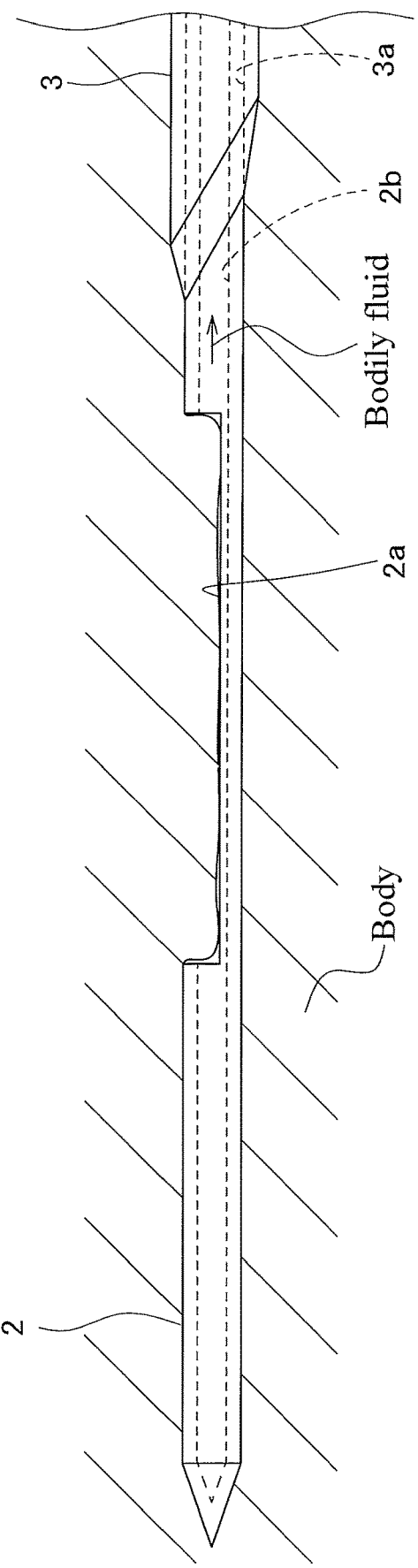
FIG.6A
FIG.6B

BIOPSY NEEDLE DEVICE

BACKGROUND

The present disclosure relates to a biopsy needle device to be used for sampling of biological tissue.

Biopsy needle devices are known that comprise an internal needle having a recess on the outer periphery near the tip, a cylindrical external needle fitting around the internal needle in a freely slidable manner in the lengthwise direction, an internal needle holding member that holds the base end section of the internal needle, an external needle holding member that holds the base end section of the external needle, an enclosure that houses the internal needle holding member and the external needle holding member in a free back-and-forth manner, a retracting device that retracts the internal needle holding member and the external needle holding member, an internal needle locking device that locks the retracted internal needle holding member at a prescribed trigger standby position, an external needle locking, device that locks the retracted external needle holding member at a prescribed trigger standby position, an unlocking operation device that unlocks the internal needle locking device and the external needle locking device in that order, an internal needle trigger spring that is energized in response to retraction of the internal needle holding member and triggers the internal needle in the forward direction in response to unlocking operation of the internal needle locking device, and an external needle trigger spring that is energized in response to retraction of the external needle holding member and triggers the external needle in the forward direction in response to unlocking operation of the external needle locking device, whereby triggering of the external needle accomplishes cutting and sampling of the biological tissue that has been drawn into the recess of the internal needle after triggering of the internal needle (see Japanese Published Examined Patent Application No. H6-28663, for example). This type of biopsy needle device allows sampling of biological tissue to be accomplished in a convenient manner simply by inserting the internal needle and external needle into the body and then carrying out triggering of the internal needle and triggering of the external needle in that order.

SUMMARY

However, with the biopsy needle device of Japanese Published Examined Patent Application No. H6-28663 it is assumed that the biological tissue will automatically be drawn into the recess of the internal needle after triggering of the internal needle, and when the biological tissue is not automatically drawn into the recess of the internal needle, it has been impossible to sample the necessary amount of biological tissue even by triggering the external needle. Moreover, while the biopsy needle device of Japanese Published Examined Patent Application No. H6-28663 allows sampling of biological tissue, sampling of bodily fluids has been more difficult.

An exemplary aspect of the present disclosure solves these problems in light of the circumstances described above. A biopsy needle device according to an exemplary aspect of the disclosure includes an internal needle having a recess on the outer periphery near the tip, a cylindrical external needle fitting around the internal needle in a freely slidable manner in the lengthwise direction, an internal needle holding member that holds the base end section of the internal needle, an external needle holding member that holds the base end section of the external needle, an enclosure that houses the internal needle holding member and the external needle holding member in a free back-and-forth manner, a retracting device that retracts the internal needle holding member and the external needle holding member, an internal needle locking device that locks the retracted internal needle holding member at a prescribed trigger standby position, an external needle locking device that locks the retracted external needle holding member at a prescribed trigger standby position, an unlocking operation device that unlocks the internal needle locking device and the external needle locking device in that order, an internal needle trigger spring that is energized in response to retraction of the internal needle holding member and triggers the internal needle in the forward direction in response to unlocking operation of the internal needle locking device, and an external needle trigger spring that is energized in response to retraction of the external needle holding member and triggers the external needle in the forward direction in response to unlocking operation of the external needle locking device, the device being such that biological tissue that has been drawn into the recess after triggering of the internal needle is cut and sampled by triggering of the external needle, wherein the internal needle is a cylindrical needle having a hollow section, the internal needle holding member comprises a cylinder that communicates with the recess through the hollow section of the internal needle, a piston internally mounted in the cylinder in a free back-and-forth manner, a piston locking device that locks the piston at a prescribed retracted standby position, and a piston retraction spring that is energized in response to retraction of the internal needle holding member, and retracts the piston relative to the cylinder in response to unlocking operation of the piston locking device, and the unlocking operation device is able to unlock the internal needle locking device, the piston locking device and the external needle locking device in that order, and when the piston retraction spring retracts the piston in response to unlocking operation of the piston locking device after triggering of the internal needle in response to unlocking operation of the internal needle locking device, negative pressure is generated in the recess of the internal needle causing biological tissue to be suctioned into the recess, after which the external needle is triggered in response to unlocking operation of the external needle locking device, whereby the biological tissue that has been drawn into the recess is cut and sampled.

A biopsy needle device according to an exemplary aspect of the disclosure includes an internal needle having a recess on the outer periphery near the tip, a cylindrical external needle fitting around the internal needle in a freely slidable manner in the lengthwise direction, an internal needle holding member that holds the base end section of the internal needle, an external needle holding member that holds the base end section of the external needle, an enclosure that houses the internal needle holding member and the external needle holding member in a free back-and-forth manner, a retracting device that retracts the internal needle holding member and the external needle holding member, an internal needle locking device that locks the retracted internal needle holding member at a prescribed trigger standby position, an external needle locking device that locks the retracted external needle holding member at a prescribed trigger standby position, an unlocking operation device that unlocks the internal needle locking device and the external needle locking device in that order, an internal needle tugger spring that is energized in response to retraction of the internal needle holding member and triggers the internal needle in the forward direction in response to unlocking operation of the internal needle locking device, and an external needle trigger spring that is energized in response to retraction of the external needle holding member and triggers the external needle in the forward direction in response to unlocking operation of the external needle locking device, the device being such that biological tissue that has been drawn into the recess after triggering of the internal needle is cut and sampled by triggering of the external needle, wherein the internal needle is a cylindrical needle having a hollow section, the internal needle holding member comprises a cylinder that communicates with the recess through the hollow section of the internal needle, a piston internally mourned in the cylinder in a free back-and-forth manner, and a piston retraction spring that can energize the piston in the direction of retraction relative to the cylinder, a piston locking device that locks the piston at a prescribed retracted standby position, the enclosure comprises a piston stopper that restricts retraction of the piston during retraction of the internal needle holding member and energizes the piston retraction spring while advancing the piston relative to the cylinder, and the unlocking operation device is able to unlock the internal needle locking device, the piston locking device and the external needle locking device in that order, and when the piston retraction spring retracts the piston in response to unlocking operation of the piston locking device after triggering of the internal needle in response to unlocking operation of the internal needle locking device, negative pressure is generated in the recess of the internal needle causing biological tissue to be suctioned into the recess, after which the external needle is triggered in response to unlocking operation of the external needle locking device, whereby the biological tissue that has been drawn into the recess is cut and sampled.

An exemplary aspect of the disclosure also includes a bodily and sampling confirmation window that allows the interior of the cylinder to be viewed from outside the enclosure.

According to above exemplary aspect of the disclosure, retraction of the piston by the piston retraction spring in response to unlocking operation of the piston locking device, after triggering of the internal needle, causes negative pressure to be generated in the recess of the internal needle, suctioning biological tissue into the recess, and thereby allowing the biological tissue that has been drawn into the recess to be reliably cut and sampled by the subsequently triggered external needle, so that the likelihood of failure in sampling of biological tissue can be drastically reduced compared to a conventional biopsy needle device which relies on the biological tissue being automatically drawn into the recess of the internal needle. Furthermore, due to the negative pressure generated in the recess of the internal needle, bodily fluid is suctioned into the hollow section of the internal needle or into the cylinder, thereby allowing bodily fluid to be sampled simultaneously with biological tissue.

According to an exemplary aspect of the disclosure, which includes a piston stopper that restricts retraction of the piston during, retraction of the internal needle holding member and energizes the piston retraction spring while advancing the piston relative to the cylinder, it is possible to achieve movement of the piston and energizing of the piston refraction spring in response to retraction of the internal needle holding member, with a simple construction.

According to an exemplary aspect of the disclosure, it is possible to confirm the state of sampling of bodily fluid through the bodily fluid sampling confirmation window, from outside the enclosure.

BRIEF DESCRIPTION OF THE DRAWINGS

FIG. 6(A) is a lateral cross-sectional view showing the piston-retracted state of a biopsy needle device according to an embodiment of the present disclosure, and FIG. 6(B) is a magnified side view showing the needle tip section in the same state.

DETAILED DESCRIPTION OF EMBODIMENTS

Figure 1:
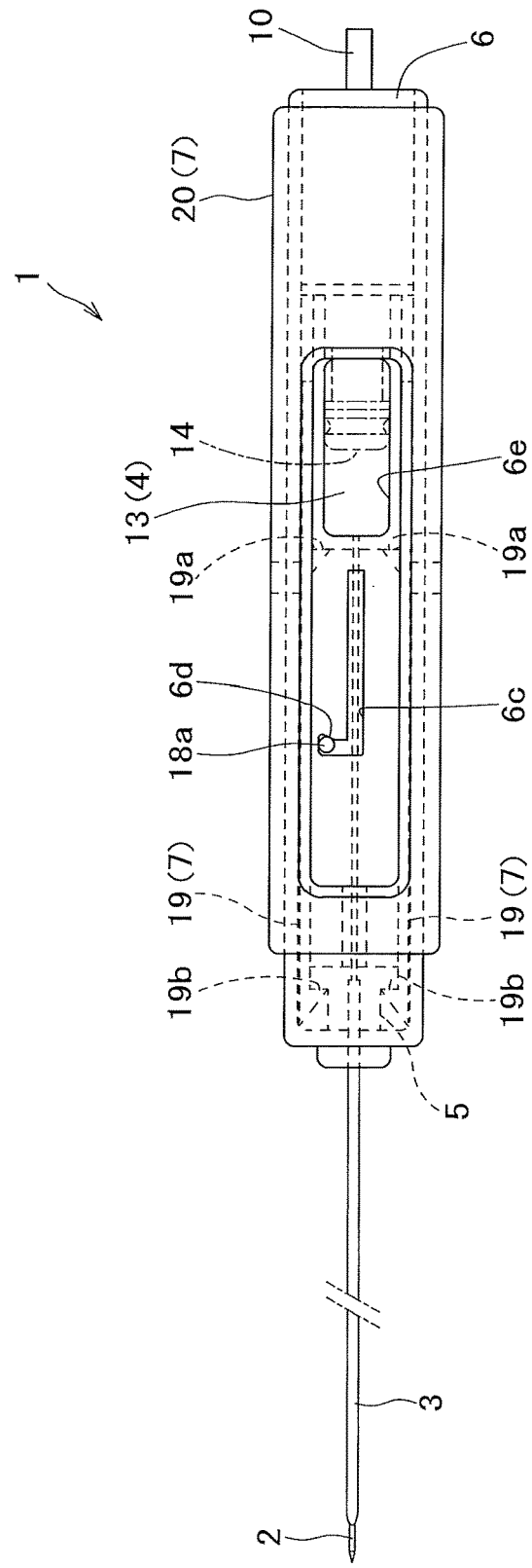
FIG. 1 is a plan view showing the initial state of a biopsy needle device according to an embodiment of the present disclosure.

An embodiment of the present disclosure will now be described with reference to the accompanying drawings. In the drawings, 1 is a biopsy needle device to be used when sampling biological tissue, the biopsy needle device 1 comprising internal needle 2 having a recess 2a on the outer periphery near the tip, a cylindrical external needle 3 fitting around the internal needle 2 in a freely slidable manner in the lengthwise direction, an internal needle holding member 4 that holds the base end section of the internal needle 2, an external needle holding member 5 that holds the base end section of the external needle 3 an enclosure 6 that houses the internal needle holding member 4 and the external needle holding member 5 in a free back-and-forth manner, a retracting device that retracts the internal needle holding member 4 and the external needle holding member 5, an internal needle locking device 8 that locks the retracted internal needle holding member 4 at a prescribed trigger standby position, an external needle locking device 9 that locks the retracted external needle holding member 5 at a prescribed trigger standby position, an unlocking operation device 10 that unlocks the internal needle locking device 8 and the external needle locking device 9 in that order, an internal needle trigger spring 11 that is energized in response to retraction of the internal needle holding member 4 and triggers the internal needle 2 in the forward direction in response to unlocking operation of the internal needle locking device 8, and an external needle trigger spring 12 that is energized in response to retraction of the external needle holding member 5 and triggers the external needle 3 in the forward direction in response to unlocking operation of the external needle locking device 9, whereby triggering of the external needle 3 accomplishes cutting and sampling of the biological tissue that has been drawn into the recess 2a of the internal needle 2 after triggering of the internal needle 2.

In the biopsy needle device 1 according to an embodiment of the present disclosure, the internal needle 2 is a cylindrical needle having a hollow section 2b. The internal needle holding member 4 comprises a cylinder 13 that communicates with the recess 2a through the hollow section 2b of the internal needle 2, a piston 14 internally mounted in the cylinder 13 in a free back-and-forth manner, a piston retraction spring 15 that is able to energize the piston 14 in the direction of retraction with respect to the cylinder 13, and a piston locking device 16 that locks the piston 14 in a prescribed retracted standby position. The enclosure 6 comprises a piston stopper 17 that restricts retraction of the piston 14 during retraction of the internal needle holding member 4 and energizes the piston retraction spring 15 while advancing the piston 14 relative to the cylinder 13. Moreover, the construction is such that the unlocking operation device 10 is able to unlock the internal needle locking device 8, the piston locking device 16 and the external needle locking device 9 in that order, and such that, after triggering of the internal needle 2 in response to unlocking operation of the internal needle locking device 8, the piston 14 is retracted by the piston retraction spring 15 in response to unlocking operation of the piston locking device 16, whereby negative pressure is generated in the recess 2a of the internal needle 2 resulting in suction of biological tissue into the recess 2a, after which an external needle 3 is triggered in response to unlocking operation of the external needle locking device 9, thereby cutting and sampling the biological tissue which has been drawn into the recess 2a. The parts and device used in the biopsy needle device 1 will now be described in detail.

The internal needle 2 is a cylindrical needle having a hollow section 2b, the tip section thereof blocking the hollow section 2b while being sharp so as to be able to be inserted into the body. The internal needle 2 has a recess 2a on the outer periphery near the tip section. The recess 2a serves to draw in and sample biological tissue after inserted into the body. The hollow section 2b of the internal needle 2 opens upward through the recess 2a.

The external needle 3 is also a tubular needle having a hollow section 3a and is fitted around the internal needle 2 in a freely slidable manner in the lengthwise direction. The tip section of the external needle 3 opens to permit protrusion of the internal needle 2 and has a sharp form so as to allow its insertion into the body and cutting and sampling of the biological tissue that has been drawn into the recess 2a of the internal needle 2.

The enclosure 6 is partitioned into an anterior chamber 6a and a posterior chamber 6b, and the internal needle holding member 4 is housed in a free back-and-forth manner in the posterior chamber 6b. The internal needle holding member 4 comprises a cylinder 13 that holds the base end section of the internal needle 2 and communicates with the recess 2a, through the hollow section 2b. The interior of the cylinder 13 houses a free back-and-forth moving piston 14 and a piston retraction spring 15 comprising a compression coil spring capable of energizing the piston 14 in the direction of retraction with respect to the cylinder 13. The cylinder 13 of this embodiment is formed of a transparent resin, and its interior is visible.

Between the cylinder 13 and the piston 14 there is provided a piston locking device 16 that locks the piston 14 at a prescribed retracted standby position. The piston locking device 16 of this embodiment comprises a locking peg 14b formed partway along a locking rod 14a that extends backward from the piston 14, and a locking hole 13a formed in the barrel of the cylinder 13. The unlocking operation is carried out by lifting the tip section of the locking rod 14a upward with a second unlocking protrusion 10a of the unlocking operation device 10.

The external needle holding member 5 is housed in a free back-and-forth manner in the anterior chamber 6a of the enclosure 6, and holds the base end section of the external needle 3. The external needle holding member 5 has a tubular extension 5a formed extending backward, and a flange section 5b formed at the tip thereof engages with an external needle manual retracting tool 18, from the rear, As shown in FIG. 1, the external needle manual retracting tool 18 has a manipulating projection 18a that protrudes to the top side of the enclosure 6, through an L-shaped guide hole 6c formed in the enclosure 6. The manipulating projection 18a is normally located in a locking groove 6d formed on the front end of the guide hole 6c, whereby the manipulating projection 18a restricts back-and-forth movement of the external needle manual retracting tool 18 while also allowing manual retraction of the external needle 3 by backward manipulation from the locking groove 6d along the guide hole 6c, after biological tissue has been sampled and when the biological tissue is removed from the recess 2a of the internal needle 2. The biopsy needle device 1 comprises a spring that energizes the manipulating projection 18a toward the locking groove 6d (not shown in the drawing).

The enclosure 6 is a resin case that houses the different members and device of the biopsy needle device 1. The internal needle 2 and the external needle 3 protrude toward the front from the top side of the enclosure 6, and the rear end of the unlocking operation device 10 protrude from the rear side of the enclosure 6. Also, the manipulating projection 18a of the external needle manual retracting tool 18 protrudes outward on the top side of the enclosure 6, and a bodily fluid sampling confirmation window 6e is formed allowing the interior of the cylinder 13 to be viewed from the outside the enclosure 6.

The retracting device 7 is provided for retraction of the internal needle holding member 4 and the external needle holding member 5 to the trigger standby position, prior to sampling of biological tissue. The retracting device 7 of this embodiment is constructed comprising a pair of left and right interior slide members 19 provided in a freely slidable manner forward and backward along the left and right inner sides of the enclosure 6, and an exterior slide member 20 provided in a freely slidable manner forward and backward along the top side and the left and right outer sides of the enclosure 6.

In the interior slide members 19 there are formed an engaging peg 19a that engages with the front end of the internal needle holding member 4 (cylinder 13) from the front, an engaging peg 19b that engages with the front end of the external needle holding member 5 from the front, and a joint 19c protruding from the enclosure 6 and connected to the exterior slide member 20. When the exterior slide member 20 is slid in the direction of retraction with respect to the enclosure 6, the internal needle holding member 4 and the external needle holding member 5 are retracted to their trigger standby positions through the interior slide members 19.

For this embodiment, the piston 14 is moved to the retracted standby position in response to retraction of the internal needle holding member 4. That is, the enclosure 6 of this embodiment comprises a piston stopper 17 that protrudes from the rear end of the posterior chamber 6b to the piston 14. The piston stopper 17 restricts retraction of the piston 14 during retracting of the internal needle holding member 4, and advances the piston 14 to the retracted standby position relative to the cylinder 13, while compressively energizing the piston retraction spring 15.

The internal needle locking device 8 locks the retracted internal needle holding member 4 (cylinder 13) at the prescribed trigger standby position. The internal needle locking device 8 of this embodiment comprises a locking peg 4a extending backward from the bottom end of the internal needle holding member 4, and a catch 6f formed on the enclosure 6.

The external needle locking device 9 locks the retracted external needle holding member 5 at the prescribed trigger standby position. The external needle locking device 9 of this embodiment comprises a locking peg 5c extending backward from the bottom end of the external needle holding member 5, and a catch 6g formed on the enclosure 6.

The unlocking operation device 10 is able to unlock the internal needle locking device 8, the piston locking device 16 and the external needle locking device 9 in that order. The unlocking operation device 10 of this embodiment is a rod member housed in a freely slidable manner forward and backward at the bottom of the enclosure 6, in a manner so that the internal needle locking device 8, the piston locking device 16 and the external needle locking device 9 are unlocked in that order, by pushing and pulling the rear end protruding from the enclosure 6.

More specifically, a first unlocking protrusion 10b, a second unlocking protrusion 10a and a third unlocking protrusion 10c are formed in the unlocking operation device 10, in that order from the rear end, and with a first push (low pressing force), the first unlocking protrusion 10b lifts the locking peg 4a of the internal needle holding member 4 upward, unlocking the internal needle locking device 8. Because the first unlocking protrusion 10b and the catch 6f of the enclosure 6 are slightly offset from left to right, sliding operation of the unlocking operation device 10 is not restricted by the catch 6f.

When the unlocking operation device 10 is then pulled, the second unlocking protrusion 10a lifts the locking peg 14b of the piston 14 through the locking rod 14a, unlocking the piston locking device 16. Because the second unlocking protrusion 10a and the locking peg 4a of the internal needle holding member 4 are slightly offset from left to right, sliding operation of the unlocking operation device 10 is not restricted by the locking peg 4a.

Finally, one more pushing operation of the unlocking operation device 10 (high pressing force) causes the third unlocking protrusion 10c to lift the locking peg 5c of the external needle holding member 5, unlocking the external needle locking device 9.

The internal needle trigger spring 11 is a compression coil spring, inserted between the rear end of the internal needle holding member 4 (cylinder 13) and the rear wall of the enclosure 6. The internal needle trigger spring 11 is energized in response to retraction of the internal needle holding member 4, the internal needle 2 being triggered in the forward direction in response to unlocking operation of the internal needle locking device 8.

The external needle trigger spring 12 is a compression coil spring, inserted between the rear end of the external needle holding member 5 and the external needle manual retracting tool 18. The external needle trigger spring 12 is energized in response to retraction of the external needle holding member 5, the external needle 3 being triggered in the forward direction in response to unlocking operation of the external needle locking device 9.

The operation and action of a biopsy needle device 1 according to an embodiment of the present disclosure will now be described with reference to the accompanying drawings.

Figure 2:
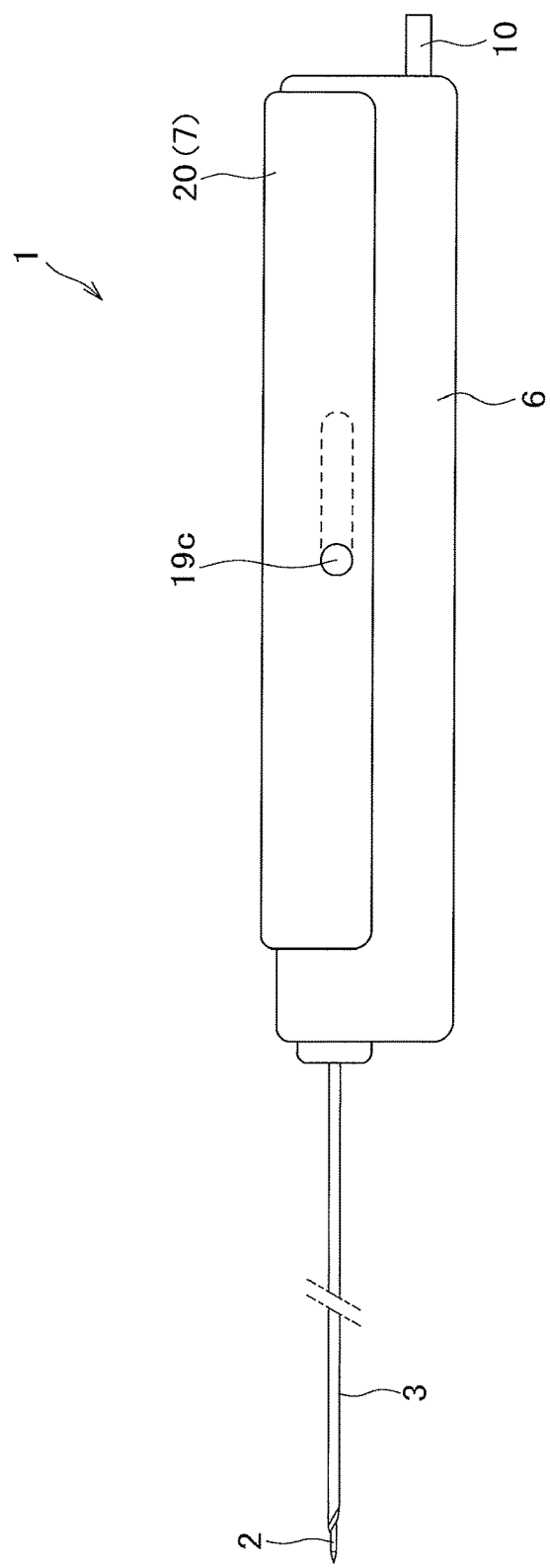
FIG. 2 is a side view showing the initial state of a biopsy needle device according to an embodiment of the present disclosure.
Figure 3A:
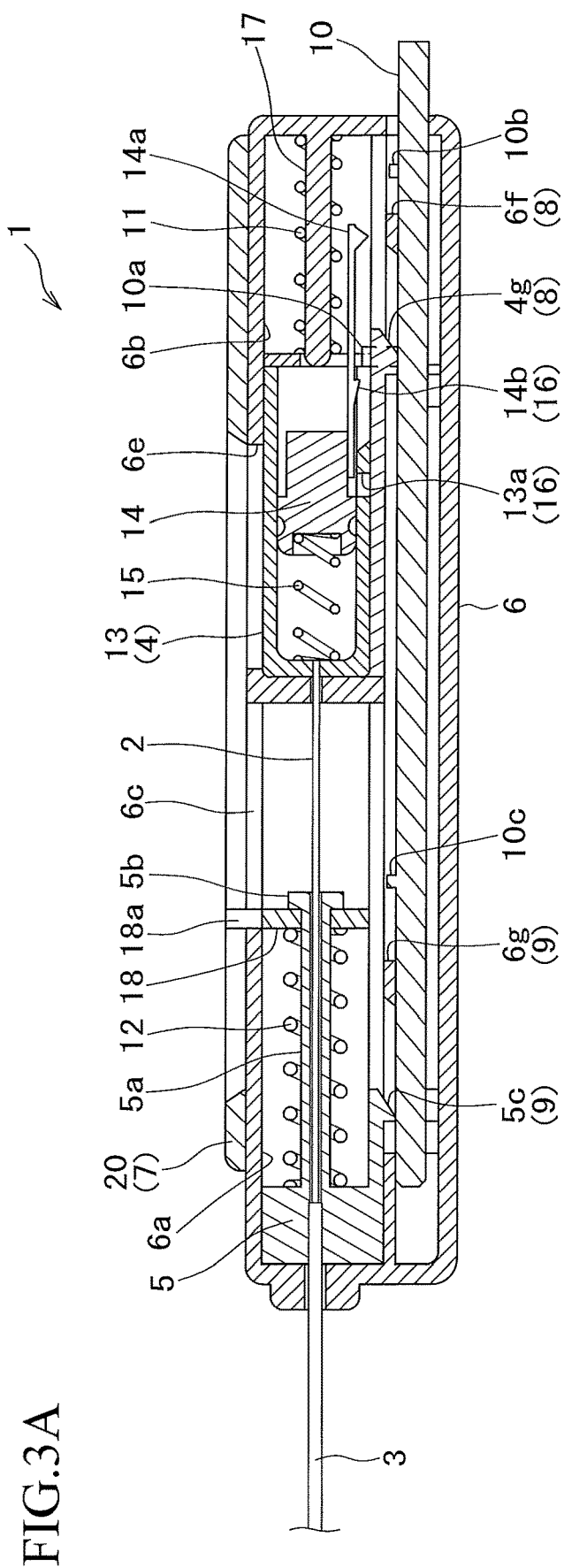
FIG. 3(A) is a lateral cross-sectional view showing the initial state of a biopsy needle device according to an embodiment of the disclosure.
Figure 3B:
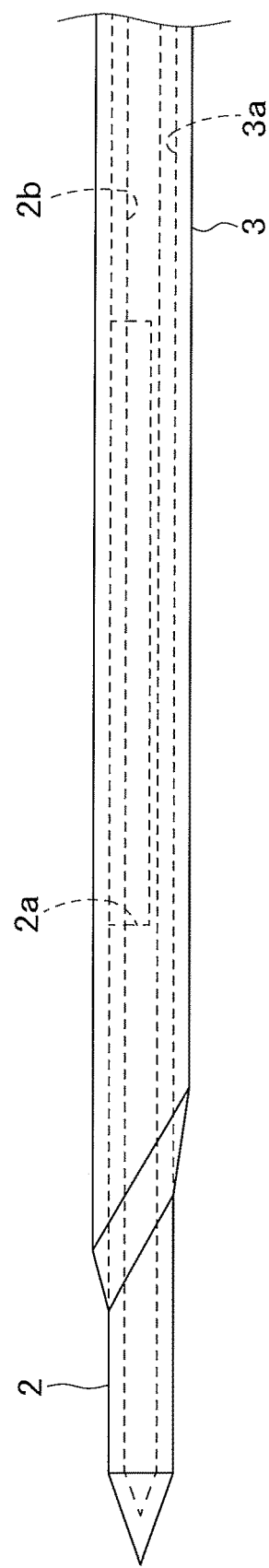
FIG. 3(B) is a magnified side view showing the needle tip section in the same state.

As shown in FIGS. 1 to 3, the biopsy needle device 1 in its initial state has the manipulating projection 18a of the external needle manual retracting tool 18 located in the locking groove 6d of the enclosure 6, and the internal needle holding member 4 and the external needle holding member 5 at their advanced positions, with the piston 14 at tie retracted position with respect to the cylinder 13, and all of the springs 11, 12, 15 in their released state.

Figure 4A:
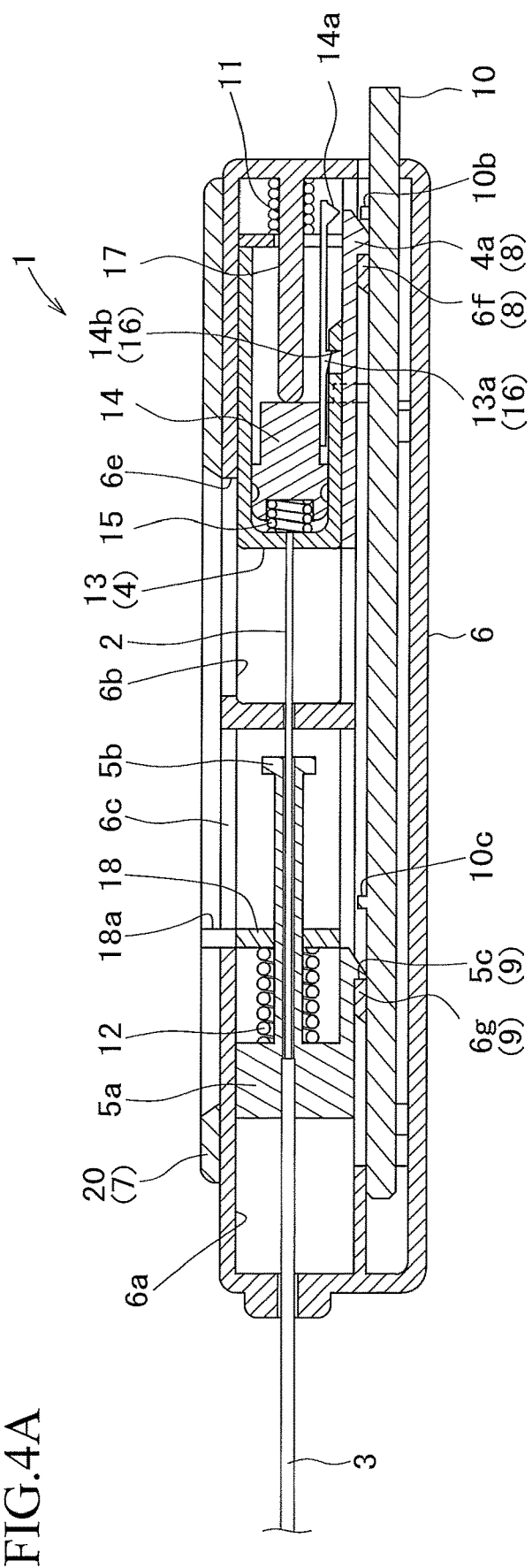
FIG. 4(A) is a lateral cross-sectional view showing the energized state of a biopsy needle device according to an embodiment of the present disclosure.
Figure 4B:
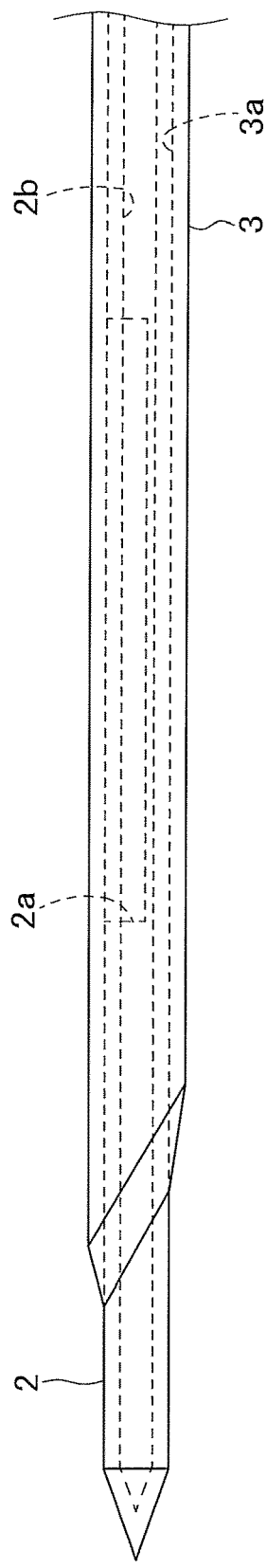
FIG. 4(B) is a magnified side view showing the needle tip section in the same state.

With the biopsy needle device 1 in its initial state, sliding the exterior slide member 20 backward causes the interior slide members 19 to retract the internal needle holding member 4 and the external needle holding member 5. When the internal needle holding member 4 and the external needle holding member 5 are retracted, the internal needle trigger spring 11 and the external needle trigger spring 12 become energized, while the internal needle locking device 8 and the external needle, locking device 9 become locked upon reaching the prescribed trigger standby position. Also, the piston 14 contacts with the piston stopper 17 as the internal needle holding member 4 is retracted, whereby the piston 14 advances relative to the cylinder 13 to the retracted standby position, while the piston retraction spring 15 is compressively energized and locked by the piston locking device 16. FIG. 4 shows the state of complete energizing of the springs 11, 12, 15, wherein only the tip section of the internal needle 2 protrudes from the tip of the external needle 3, and the recess 2a is positioned in the external needle 3.

Figure 5A:
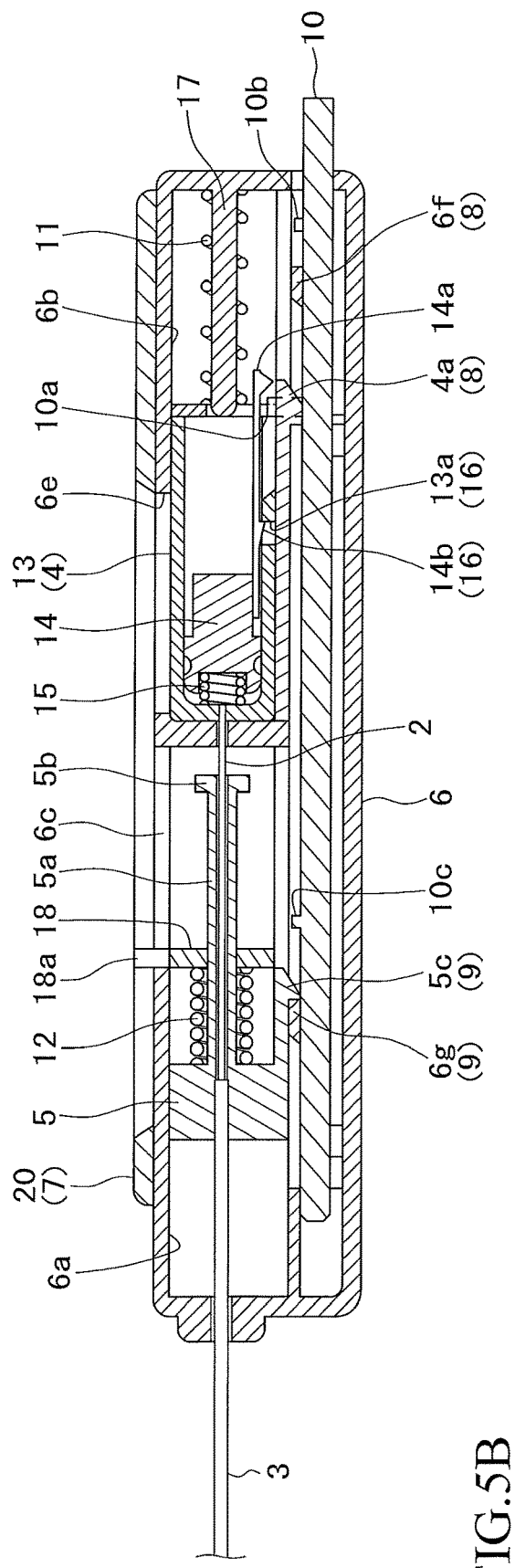
FIG. 5(A) is a lateral cross-sectional view showing the internal needle-triggered state of a biopsy needle device according to an embodiment of the present disclosure.
Figure 5B:
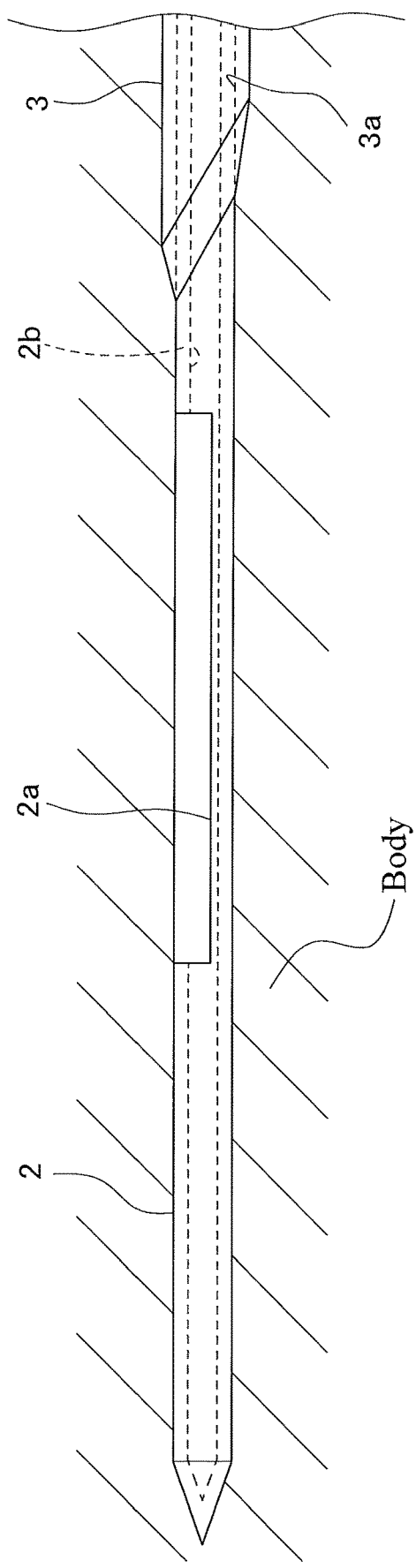
FIG. 5(B) is a magnified side view showing the needle tip section in the same state.

The internal needle 2 and the external needle 3 are then inserted into the body in the state shown in FIG. 4. After the tip sections of the internal needle 2 and the external needle 3 have reached the prescribed tissue-sampling location, pushing of the unlocking operation device 10 is initiated. When the unlocking operation device 10 is pushed, the first unlocking protrusion 10b lifts the locking peg 4a of the internal needle holding member 4, unlocking the internal needle locking device 8. When the internal needle locking device 8 becomes unlocked, the internal needle holding member 4 advances by the energized force of the internal needle trigger spring 11, so that the internal needle 2 that is integral with the internal needle holding member 4 is triggered in the forward direction. As shown in FIG. 5, triggering of the internal needle 2 causes the leading edge of the internal needle 2 to be ejected from the tip of the external needle 3, so that the recess 2a of the internal needle 2 becomes exposed inside the biological tissue.

The unlocking operation device 10 is then pulled back. When the unlocking operation device 10 is pulled, the second unlocking protrusion 10c lifts the locking rod 14a of the piston 14, unlocking the piston locking device 16. When the piston locking device 16 is unlocked, the piston 14 retracts with respect to the cylinder 13 by the energized force of the piston retraction spring 15. As shown in FIG. 6 retraction of the piston 14 generates negative pressure in the recess 2a of the internal needle 2 that is in communication with the cylinder 13 through the hollow section 2b, so that biological tissue is suctioned into the recess 2a, while bodily fluid is suctioned into the cylinder 13 through the hollow section 2b of the internal needle 2. The bodily fluid suctioned into the cylinder 13 can be visually confirmed through the bodily fluid sampling confirmation window 6e of the enclosure 6.

Figure 7A:
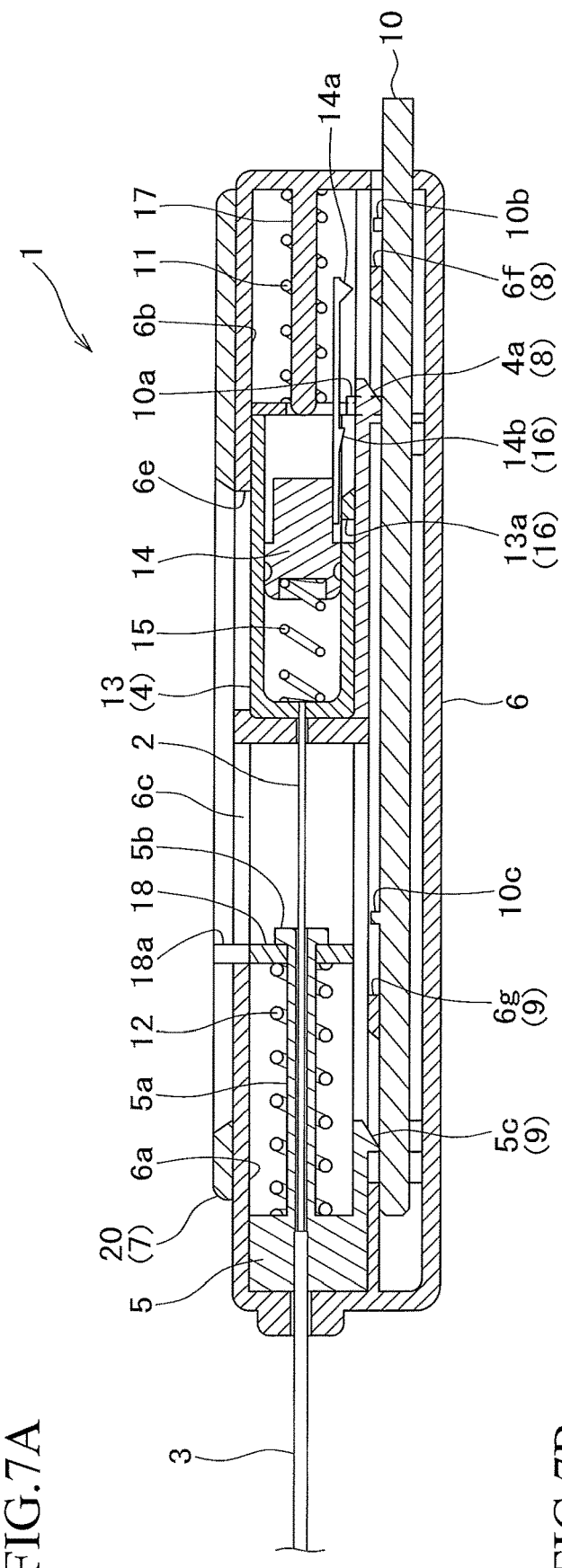
FIG. 7(A) is a lateral cross-sectional view showing the external needle-triggered state of a biopsy needle device according to an embodiment of the present disclosure.
Figure 7B:
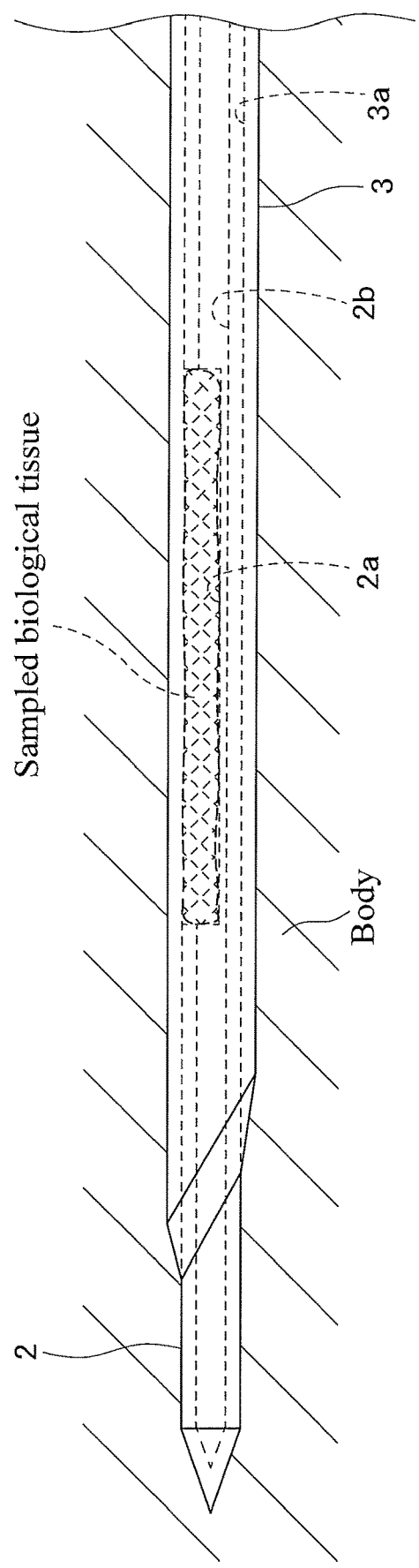
FIG. 7(B) is a magnified side showing the needle tip section in the same state.

The unlocking operation device 10 is then pushed again. When the unlocking operation device 10 is pushed again, the third unlocking protrusion 10c lifts the locking peg 5c of the external needle holding member 5, unlocking the external needle locking device 9. When the external needle locking device 9 becomes unlocked, the external needle holding member 5 advances by the energized force of the external needle trigger spring 12, so that the external needle 3 that is integral with the external needle holding member 5 is triggered in the forward direction. As shown in FIG. 7, when the external needle 3 is triggered, the tip of the external needle 3 advances along the outer periphery of the internal needle 2, so that the biological tissue drawn into the recess 2a of the internal needle 2 is cut and sampled.

Figure 8A:
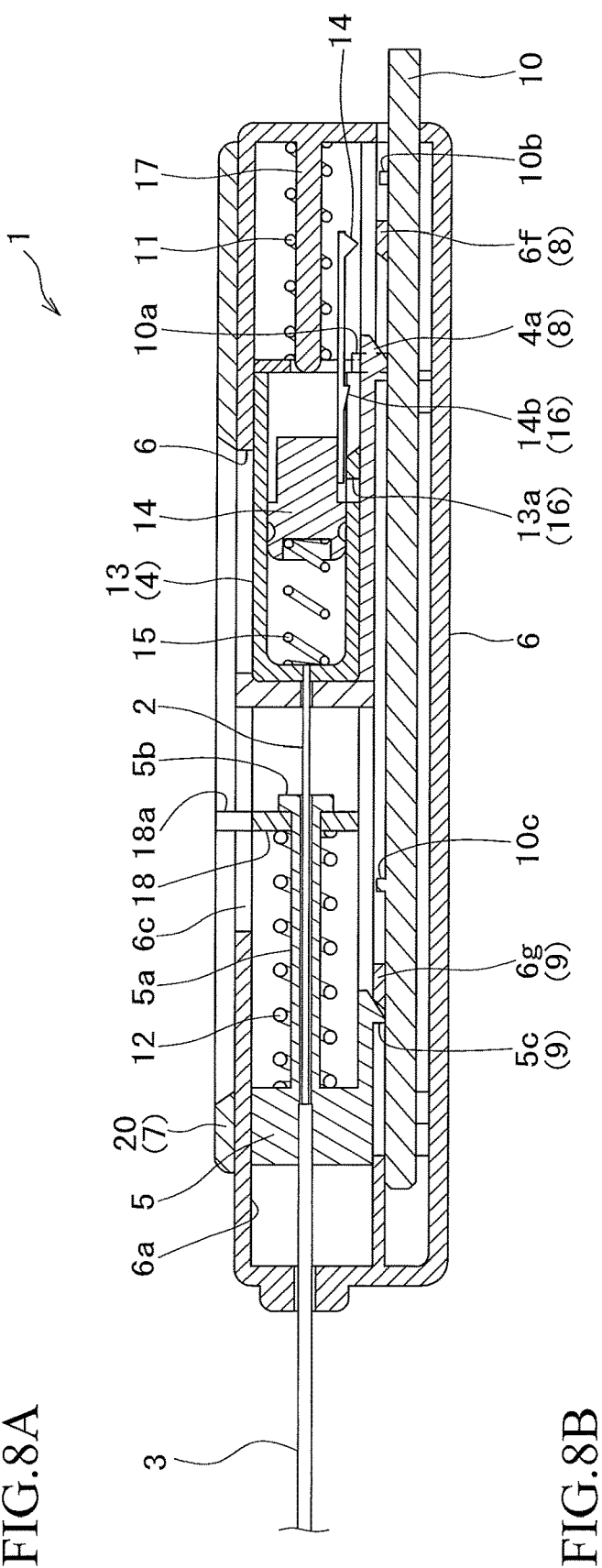
FIG. 8(A) is a lateral cross-sectional view showing the biological tissue-removed state of a biopsy needle device according to an embodiment of the present disclosure.
Figure 8B:
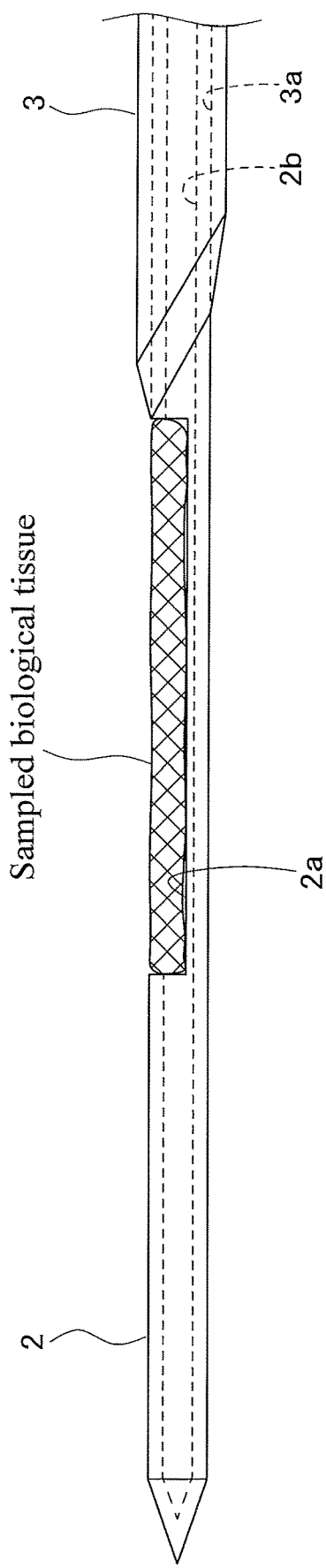
FIG. 8(B) is a magnified side view showing the needle tip section in the same state.

After triggering of the external needle 3, the internal needle 2 and the external needle 3 are pulled out of the body and the sampled biological tissue is removed. As shown in FIG. 8 when the biological tissue is removed, the manipulating projection 18a of the external needle manual retracting tool 18 is manipulated backward along the guide hole 6c. This manipulation causes retraction of the external needle holding member 5 and the external needle 3, resulting in exposure of the recess 2a of the internal needle 2, so that the biological tissue in the recess 2a can be removed. The bodily fluid in the cylinder 13 may be removed from the leading edge of the internal needle 2 by advance of the piston 14, or it may be removed upon disassembling the enclosure 6.

According to the embodiment having the construction described above, retraction of the piston 14 by the piston retraction spring 15 in response to unlocking operation of the piston locking device 16, after triggering of the internal needle 2, causes negative pressure to be generated in the recess 2a of the internal needle 2, suctioning biological tissue into the recess 2a, and thereby allowing the biological tissue that has been drawn into the recess 2a to be reliably cut and sampled by the subsequently triggered external needle 3, so that as a result, the likelihood of failure in sampling of biological tissue can be drastically reduced compared to a conventional biopsy needle device which relies on the biological tissue being automatically drawn into the recess 2a of the internal needle 2.

Furthermore, due to the negative pressure generated in the recess 2a of the internal needle 2, bodily fluid is suctioned into the hollow section 2b of the internal needle 2 and/or into the cylinder 13, thereby allowing bodily fluid to be sampled simultaneously with biological tissue.

In addition, since it further comprises a piston stopper 17 that restricts retraction of the piston 14 during retraction of the internal needle holding member 4 and energizes the piston retraction spring 15 while advancing the piston 14 relative to the cylinder 13, it is possible to achieve movement of the piston 14 and energizing of the piston retraction spring 15 in response to retraction of the internal needle holding member 4, with a simple construction.

Furthermore, since it comprises a bodily fluid sampling confirmation window 6e that allows the interior of the cylinder 13 to be viewed from outside the enclosure 6, it is possible to easily confirm the state of sampling of bodily fluid.

The invention claimed is:

1. A biopsy needle device comprising:
an internal needle having a recess on an outer periphery near a tip of the internal needle;
a cylindrical external needle fitting around the internal needle in a freely slidable manner in a lengthwise direction,
an internal needle holding member that holds a base end section of the internal needle,
an external needle holding member that holds a base end section of the external needle,
an enclosure that houses the internal needle holding member and the external needle holding member in a free back-and-forth manner,
a retracting device that retracts the internal needle holding member and the external needle holding member,
an internal needle locking device that locks the internal needle holding member at a prescribed trigger standby position when the internal needle holding member is retracted by the retracting device,
an external needle locking device that locks the external needle holding member at a prescribed trigger standby position when the external needle locking device is retraced by the retracting device,
an unlocking operation device that unlocks the internal needle locking device in response to a first unlocking operation and the external needle locking device in response to a third unlocking operation,
an internal needle trigger spring that is energized in response to retraction of the internal needle holding member and triggers the internal needle in a forward direction in response to the first unlocking operation of the internal needle locking device by the unlocking operation device, and
an external needle trigger spring that is energized in response to retraction of the external needle holding member and triggers the external needle in the forward direction in response to the third unlocking operation of the external needle locking device by the unlocking operation device,
the biopsy needle device being such that biological tissue that has been drawn into the recess after triggering of the internal needle is cut and sampled by triggering of the external needle, wherein:
the internal needle is a cylindrical needle having a hollow section,
the internal needle holding member comprises:
a cylinder that communicates with the recess through the hollow section of the internal needle and moves relative to the enclosure integrally with the internal needle,
a piston internally mounted in the cylinder in a free back-and-forth manner,
a piston locking device that locks the piston at a prescribed retracted standby position, and
a piston retraction spring that is energized in response to retraction of the internal needle holding member, and retracts the piston relative to the cylinder in response to a second unlocking operation in which the piston locking device is unlocked by the unlocking operation device,
the unlocking operation device is able to unlock the internal needle locking device in response to the first unlocking operation, the piston locking device in response to the second unlocking operation and the external needle locking device in response to the third unlocking operation in the order of the first, second and third unlocking operations, the first, second and third unlocking operations are started by independent operations, respectively, by the first unlocking operation, the piston and the cylinder move in the forward direction with their positional relationship maintained and relative to the enclosure so that internal pressure is maintained in the cylinder and the recess of the internal needle through the hollow section, and at the same time, the internal needle is triggered so that the recess of the internal needle is exposed, by the second unlocking operation, the piston retraction spring retracts the piston so that negative pressure is generated in the recess of the internal needle through the hollow section wherein the internal needle is in communication with the cylinder and is configured to cause biological tissue to be suctioned into the recess, and by the third unlocking operation, the biological tissue that has been drawn into the recess is cut and sampled.

2. A biopsy needle device according to claim 1, wherein:

the piston retraction spring can energize the piston in a direction of retraction relative to the cylinder, and the enclosure comprises a piston stopper that restricts retraction of the piston during retraction of the internal needle holding member by the retracting device and that energizes the piston retraction spring while advancing the piston relative to the cylinder.

3. A biopsy needle device according to claim 1, further comprising a bodily fluid sampling confirmation window that allows an interior of the cylinder to be viewed from an exterior of the enclosure.

4. A biopsy needle device according to claim 2, further comprising a bodily fluid sampling confirmation window that allows an interior of the cylinder to be viewed from an exterior of the enclosure.

5. A biopsy needle device according to claim 1, wherein a base end of the internal needle is opened so that the internal needle is in communication with the cylinder through the base end of the internal needle.

* * * * *